(12) United States Patent
Creaturo (10) Patent No.: US 9,302,050 B2
(45) Date of Patent: Apr. 5, 2016

(54) SAFETY SYRINGE AND SAFETY DOSE COMBINATION KIT AND METHODS

(71) Applicant: Parenteral Technologies, LLC, Siesta Key, FL (US)

(72) Inventor: Michael A. Creaturo, Siesta Key, FL (US)

(73) Assignee: Parenteral Technologies, LLC, Siesta Key, FL (US)

( * ) Notice: Subject to any disclaimer, the term of this patent is extended or adjusted under 35 U.S.C. 154(b) by 47 days.

(21) Appl. No.: 14/211,920

(22) Filed: Mar. 14, 2014

(65) Prior Publication Data

US 2014/0207079 A1 Jul. 24, 2014

Related U.S. Application Data

(63) Continuation-in-part of application No. 13/748,859, filed on Jan. 24, 2013.

(60) Provisional application No. 61/783,165, filed on Mar. 14, 2013.

(51) Int. Cl.
*A61M 3/00* (2006.01)
*A61M 5/31* (2006.01)
*A61M 5/00* (2006.01)
*A61M 5/315* (2006.01)
*A61M 5/28* (2006.01)

(52) U.S. Cl.
CPC ............. *A61M 5/3129* (2013.01); *A61M 5/002* (2013.01); *A61M 5/31* (2013.01); *A61M 5/31511* (2013.01); *A61M 5/284* (2013.01); *A61M 2005/3126* (2013.01); *A61M 2205/6009* (2013.01)

(58) Field of Classification Search
CPC ............. A61M 2205/6081; A61M 2005/3125; A61M 5/31556; A61M 2005/3126; A61M 2205/6063; A61M 2205/60; A61M 2205/607; A61M 5/3129; A61M 2205/6009; A61M 5/002; A61M 5/284
See application file for complete search history.

(56) References Cited

U.S. PATENT DOCUMENTS

| | | | |
|---|---|---|---|
| 6,413,241 B1 * | 7/2002 | Slishman | 604/186 |
| 2004/0024368 A1 * | 2/2004 | Broselow | 604/207 |
| 2010/0130961 A1 * | 5/2010 | Tucker | 604/518 |

* cited by examiner

*Primary Examiner* — Rebecca E Eisenberg
(74) *Attorney, Agent, or Firm* — Shumaker, Loop & Kendrick, LLP (57) ABSTRACT

A syringe including a barrel having an internal reservoir for containing a volume of medication, a plunger received within the barrel and axially moveable relative thereto to change the volume of the medication in the reservoir, a first set of indicia marked on the barrel indicating volumetric dosage of the medication calibrated based on a predetermined patient characteristic, and a second set of indicia marked on the barrel having a correlation with the first set of indicia, the second set of indicia indicating volumetric dosage of the medication calibrated based on a medication unit of measurement. A kit including a syringe and a pre-filled medication container calibrated based on a patient characteristic.

14 Claims, 10 Drawing Sheets

CROSS-SECTIONAL VIEW
I-I

CROSS-SECTIONAL VIEW
II-II

FIG. 9B

CROSS-SECTIONAL VIEW
III-III

FIG. 10B

SAFETY SYRINGE AND SAFETY DOSE COMBINATION KIT AND METHODS

CROSS-REFERENCE TO RELATED APPLICATIONS

This Continuation-in-Part application claims priority from U.S. patent application Ser. No. 13/748,859 filed Jan. 24, 2013, which claims priority from U.S. Patent Application No. 61/591,683 filed Jan. 27, 2012, this application further claims priority from U.S. Patent Application No. 61/783,165 filed Mar. 14, 2013, the entirety of each of which is incorporated by reference herein.

TECHNICAL FIELD AND BACKGROUND OF THE INVENTION

The present invention relates generally to the field of reducing errors associated with administering injectable medications, and more particularly, to medication specific syringes calibrated based on patient characteristics such as body weight and/or body surface area, as well as volumetrically calibrated medicinal injection kits including one or more of volumetrically calibrated medication/patient specific syringes, volumetrically calibrated diluent syringes and medications.

Medical Administered Errors ("MAEs") account for more deaths annually than motor vehicle accidents, breast cancer and AIDS. Studies indicate that most MAEs are attributed to administering injectable medications, with errors including administering incorrect dosages, administering the wrong medication, and administering along the wrong route. Other studies indicate that MAEs injure approximately 1.3 million people, and account for nearly 100,000 deaths, annually in the U.S. alone. Children are the most susceptible to harm due to their lower body mass, making them more sensitive to overdoses or underdoses that can result in adverse reactions, ineffective treatment, illness and even death.

Other studies indicate that MAEs occur in approximately one out of every five doses given in hospitals and that, on average, a hospital patient is subject to at least one medication error per day, with considerable variation in error rates across facilities. MAEs are attributable in large part to poor communication, misinterpreted handwriting, drug name confusion, drug strength, inaccurate dosage calculations, confusing medication labeling and packaging, lack of clinical knowledge, lack of patient understanding of drug directions, dilution procedures, fast paced and high stress environments, long working hours and fatigue, emergency procedures, etc. The financial impact to the U.S. healthcare industry as a result of MAEs is estimated to exceed $100 billion annually.

Accordingly, what is needed are apparatus and methods for significantly reducing the number of MAEs attributable to administering injectable medication.

BRIEF SUMMARY OF THE INVENTION

In one aspect, the present invention is directed to substantially reducing or eliminating MAEs associated with administering injectable medication.

In another aspect, the present invention is directed to syringe configurations that obviate the need for performing dosage and diluent calculations at the time of administering injectable medications.

In yet another aspect, provided herein are medication-specific syringe configurations calibrated based on patient-specific characteristics such as body weight and body surface area, among other patient characteristics.

In yet another aspect, provided herein are kits including one or more of patient calibrated, medication-specific syringes, volumetrically calibrated diluent syringes, and medication vials.

To achieve the foregoing and other aspects and advantages, in one embodiment the present invention provides a syringe including a barrel having an internal reservoir for containing a volume of medication, a plunger received within the barrel and axially moveable relative thereto to change the volume of the medication in the reservoir, and a first set of indicia marked on the barrel indicating volumetric dosage of the medication calibrated based on a predetermined patient characteristic.

In a further embodiment, the predetermined patient characteristic is selected from the group consisting of patient body weight and patient body surface area.

In a further embodiment, the syringe includes a second set of indicia marked on the barrel or plunger having a correlation with the first set of indicia, the second set of indicia indicating volumetric dosage of the medication calibrated based on a medication unit of measurement, wherein the medication unit of measurement is selected from the group consisting of volume, mass and concentration of the medication.

In a further embodiment, the syringe includes graduation indicia marked on the barrel or plunger correlating the volumetric dosage of the first set of indicia with the volumetric dosage of the second set of indicia.

In a further embodiment, the syringe includes indicia marked on the plunger indicating a particular medication or medication type for use with the syringe, and indicating a correlation between a unit of measurement of the medication and a unit of measurement of the predetermined patient characteristic.

In a further embodiment, the volumetric dosage of the medication calibrated based on the predetermined patient characteristic is expressed as a maximum or recommended value of the predetermined patient characteristic.

In a further embodiment, the syringe includes a needle attached to one end of the barrel and in fluid communication with the internal reservoir.

In another embodiment, provided herein is a diluent syringe for reconstituting medication including a barrel having an internal reservoir for containing a volume of diluent, a plunger received within the barrel and axially moveable relative thereto to change the volume of the diluent in the reservoir, and indicia marked on the barrel or plunger indicating a calibrated volumetric dosage of the diluent.

In a further embodiment, the diluent syringe is volumetrically calibrated based upon the predetermined medication characteristic that accompanies it within the kit.

In a further embodiment, the barrel indicia includes an annular marking around the barrel indicating a diluent fill line barrel tinting from the needle end to the diluent fill line to provide a visible indicator to the user of the volume of diluent to be drawn into the internal reservoir.

In a further embodiment, the plunger is marked with indicia indicating one or more of a particular diluent to be used with the diluent syringe and a correlation between a volumetric unit of measurement of the diluent and unit of measurement of the medication to be reconstituted with the diluent.

In yet another embodiment, provided herein is a pre-packaged medication kit including a medication syringe including a barrel having an internal reservoir for containing a volume of medication, a plunger received within the barrel and axially moveable relative thereto to change the volume of the medication in the reservoir, and a first set of indicia marked on the barrel indicating volumetric dosage of the medication calibrated based on a predetermined patient characteristic, and a pre-filled medication container containing a predetermined volume of the medication calibrated based on the predetermined patient characteristic.

In a further embodiment, the predetermined patient characteristic is selected from the group consisting of patient body weight and patient body surface area, and the medication syringe further includes a second set of indicia marked on the barrel having a correlation with the first set of indicia, the second set of indicia indicating volumetric dosage of the medication calibrated based on a medication unit of measurement.

In a further embodiment, the pre-packaged kit includes a diluent syringe for reconstituting medication including a barrel having an internal reservoir for containing a volume of diluent, a plunger received within the barrel and axially moveable relative thereto to change the volume of the diluent in the reservoir, and indicia marked on the barrel indicating a calibrated volume of the diluent, wherein the volume of the diluent is calibrated based on a predetermined characteristic of the medication to correctly reconstitute the medication for proper administration, and a pre-filled container containing a predetermined volume of diluent.

In a further embodiment, the plunger of each of the medication syringe and the diluent syringe is marked with indicia indicating the particular medication or diluent for use therewith, and wherein the plunger of the medication syringe is marked with indicia indicating a correlation between a unit of measurement of the medication and a unit of measurement of the predetermined patient characteristic, and wherein the plunger of the diluent syringe is marked with indicia indicating a correlation between diluent volume and a unit of measurement of the medication.

Embodiments of the invention can include one or more or any combination of the above features and configurations.

Additional features, aspects and advantages of the invention will be set forth in the detailed description which follows, and in part will be readily apparent to those skilled in the art from that description or recognized by practicing the invention as described herein. It is to be understood that both the foregoing general description and the following detailed description present various embodiments of the invention, and are intended to provide an overview or framework for understanding the nature and character of the invention as it is claimed. The accompanying drawings are included to provide a further understanding of the invention, and are incorporated in and constitute a part of this specification.

BRIEF DESCRIPTION OF THE DRAWINGS

These and other features, aspects and advantages of the present invention are better understood when the following detailed description of the invention is read with reference to the accompanying drawings, in which.

DETAILED DESCRIPTION OF THE INVENTION

The present invention will now be described more fully hereinafter with reference to the accompanying drawings in which exemplary embodiments of the invention are shown. However, the invention may be embodied in many different forms and should not be construed as limited to the representative embodiments set forth herein. The exemplary embodiments are provided so that this disclosure will be both thorough and complete, and will fully convey the scope of the invention and enable one of ordinary skill in the art to make, use and practice the invention. Like reference numbers refer to like elements throughout the various drawings.

The term "syringe" as used herein refers to any type of syringe or like injection apparatus for administering injectable medication, and is distinguished from the term "diluent syringe," which is used herein to refer to a syringe for reconstituting medication. The various syringes and diluent syringes described herein are volumetrically calibrated based on the particular medication to be administered and predetermined patient characteristic (e.g., body weight and/or body surface area ("BSA"), and are marked accordingly with permanent indicia to prevent misuse. The term "particular medication" is used interchangeably herein with the term "predetermined medication," and refers to a specific medication or medication type. For example, a "rapid-acting insulin" may refer to one particular medication type, while the brand names of such medications types may refer to specific medications. Thus, syringe calibrations, markings, volumes, etc. may vary based on the specification medication for use with the syringe and/or patient characteristic(s).

Each syringe is preferably substantially transparent and marked with permanent, conspicuous indicia. The indicia may include labels, embossing, stamped lettering, etc., indicating the name of the medication or medication type for use with the syringe, the patient characteristic, and in particular embodiments, volumetric or mass indicia corresponding with the patient characteristic. Each syringe preferably includes a dosage calibration scale located along the length of its respective barrel, plunger, or other part marked with indicia corresponding to the patient characteristic. Calibrating and marking the syringe based on the particular medication dosage schedule of a patient characteristic and consolidating the calibrated components within a kit allows a user (e.g., patient or clinician) to administer a manufacturer's recommended dosage of the medication, for example, according to the patient's weight, BSA or other patient characteristic, without the need for performing mathematical calculations, computations, correlations or consolidation of the correct components at the time of administering the injection.

Syringe indicia, such as the patient characteristic and correlating medication unit(s) of measurement may be provided on the syringe barrel and arranged into one or more columns. Suitable medication units of measurement include, but are not limited to, mcg, cc, IU, mg, mL, and g, and may include maximum dosages and manufacturers recommend dosages. Suitable units of measurement of patient characteristics include, but are not limited to, kg and lb for patient body weight, and $m^2$ for body surface area. Another patient characteristic unit of measurement may include body mass index.

Figure 1:
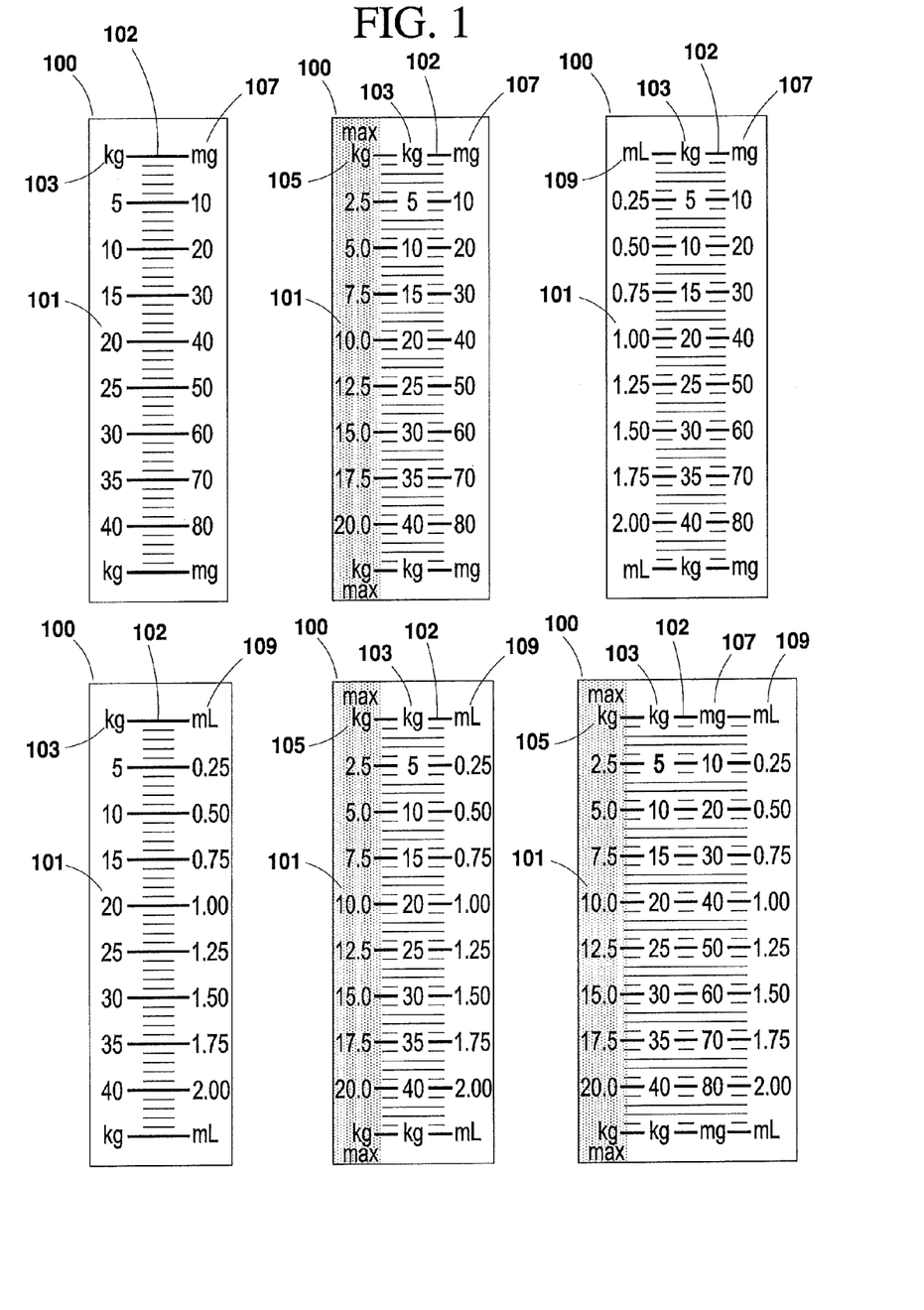
FIG. 1 illustrates various embodiments of syringe indicia indicating dosages based on correlations between patient weight and medication volume and/or mass.
Figure 2:
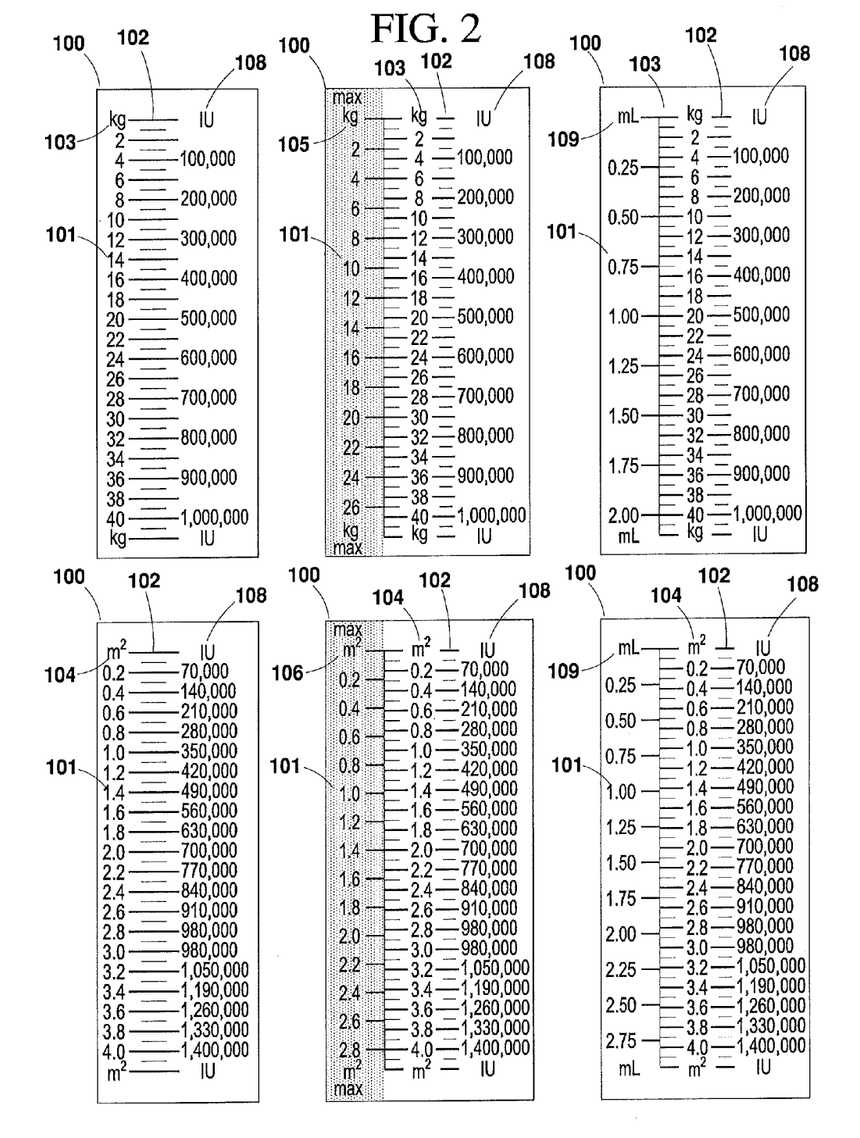
FIG. 2 illustrates various embodiments of syringe indicia indicating dosages based on correlations between patient weight, body surface area, and international units.
Figure 3:
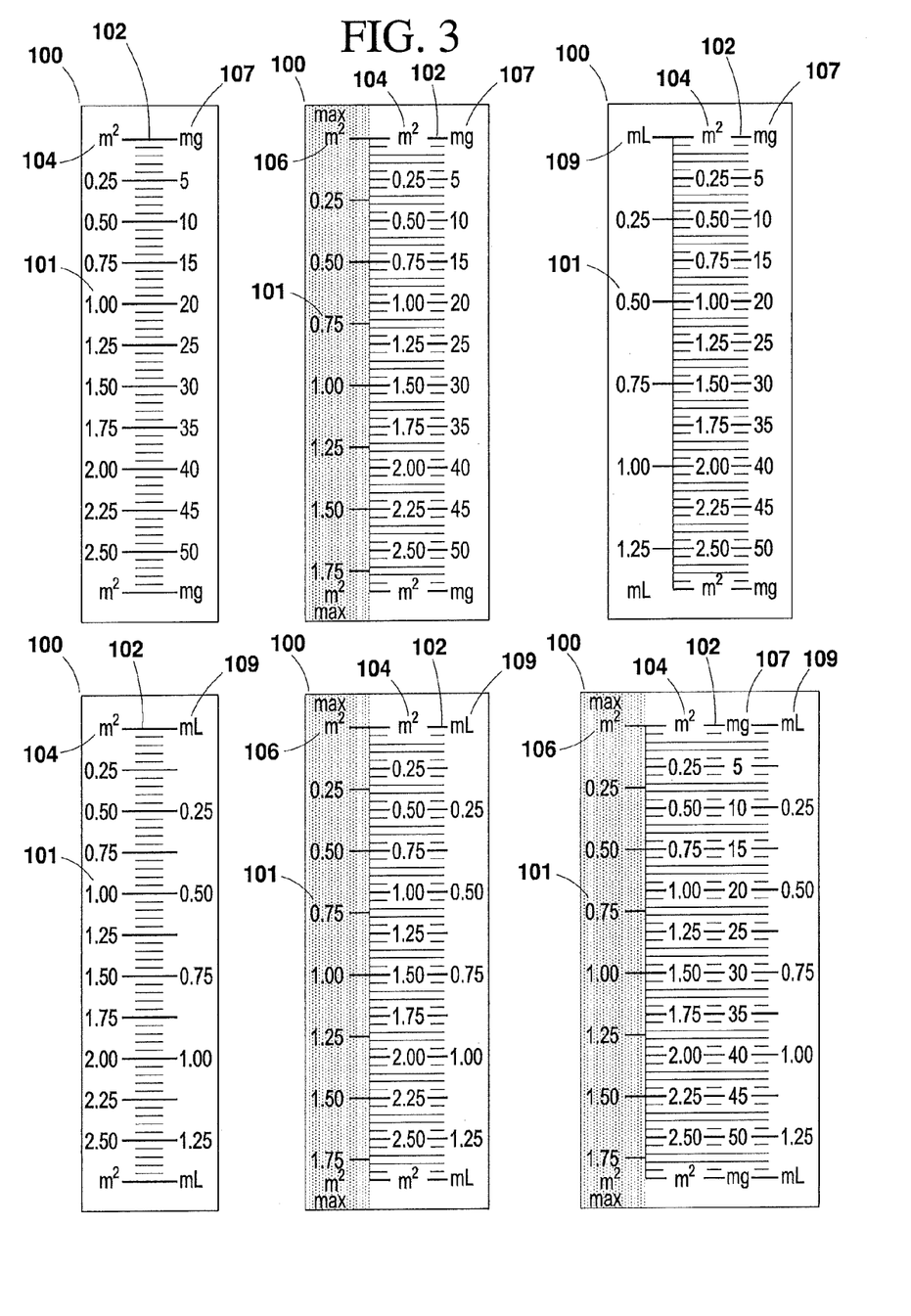
FIG. 3 illustrates various embodiments of syringe indicia indicating dosages based on correlations between body surface area and medication volume and/or mass.

Referring to FIGS. 1-3, various combinations of patient characteristic indicia (e.g., kg and $m^2$) and medication volumetric/mass indicia that may be provided on a syringe are shown. The various combinations of marked indicia show correlations between one or more of patient weight, patient BSA, medication volume, mass, international units, etc. The indicia, shown collectively at reference numeral 100, may be embossed, recessed or printed onto a label applied to the barrel. Indicia 100 generally includes measured units 101 and corresponding graduation markings 102 that correlate and correspond the patient characteristic (e.g., weight in kg shown at 103, or BSA measured in $m^2$ shown at 104, as well as lb or g) to the recommended dosage for that weight or BSA in medication units (e.g., mg 107, IU 108, mL 109 or mcg). Indicia 100 may also include patient characteristics and graduation markings 102 that correlate and correspond to the recommended maximum dosage based on the on the patient weight 105 or BSA 106. Indicia 100 may also include measured units 101 and graduation markings 102 that correspond to the strength or concentration 107 of the medication within the dosage. Indicia 100 may also include measured units 101 and graduation markings 102 that correspond to the amount of a substance 108 based on the biological activity or effect of the medication within the dosage. Indicia 100 may also include measured units 101 and graduation markings 102 that correspond to the volume 109 of medication. In a particular embodiment, the indicia 100 on the barrel includes only the patient characteristic (e.g., body weight and/or BSA) and the corresponding graduation markings 102. In another particular embodiment, the indicia 100 on the barrel includes only the medication measurement unit and corresponding graduation markings 102.

Figure 4A:
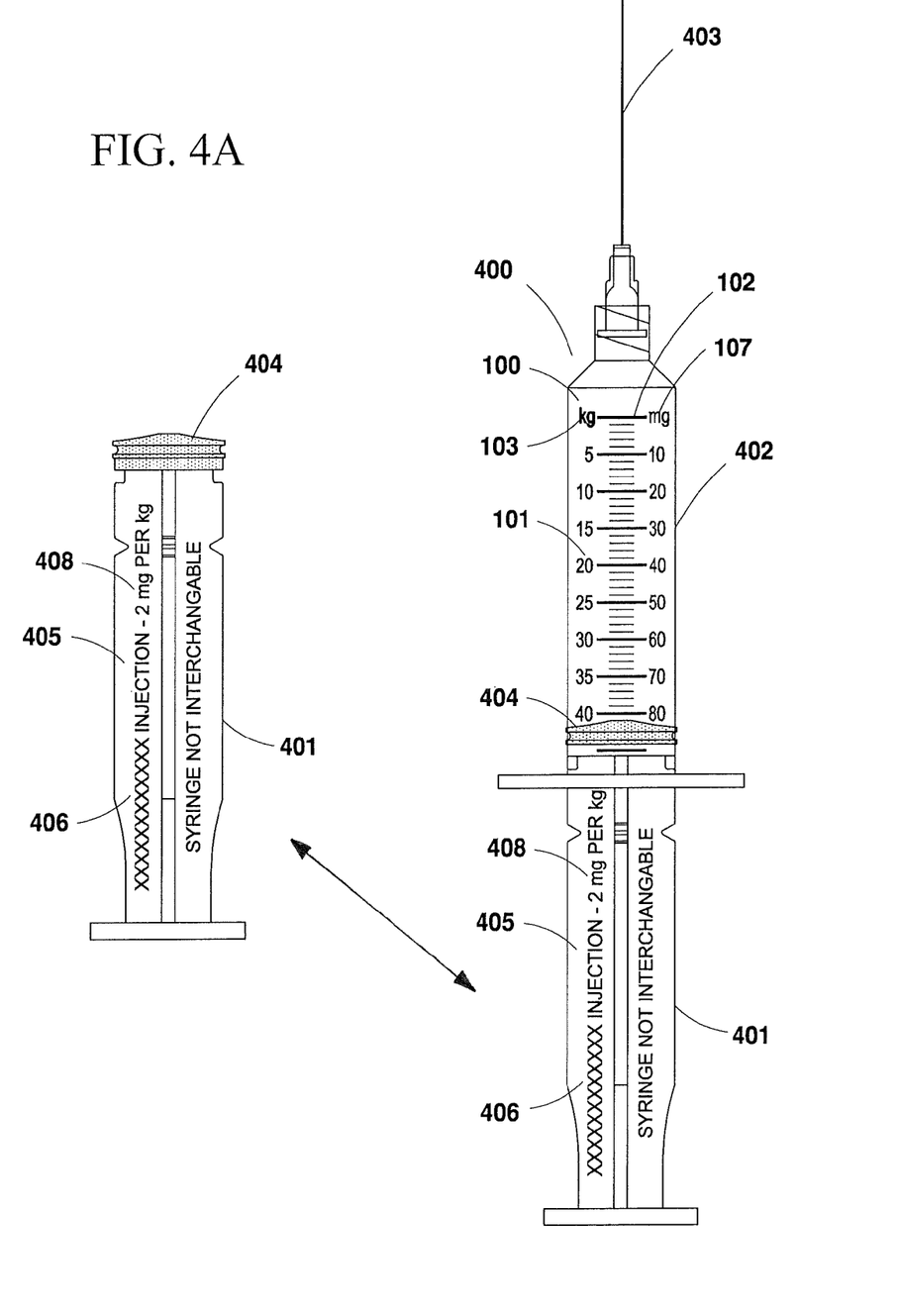
FIG. 4A illustrates one embodiment of a syringe for administering injectable medication.

Referring to FIG. 4A, a pre-calibrated syringe according to one embodiment of the invention is shown generally at reference numeral 400. Syringe 400 generally includes a plunger 401, a syringe barrel 402, and a needle 403. The syringe barrel 402 defines an internal reservoir for holding a volume of medication. The plunger 401 moves axially within the barrel 402, and an elastomeric seal 404 (e.g., cap or gasket) located at one end of the plunger 401 effects a seal between the plunger and the inner wall of the barrel such that withdrawing the plunger from the barrel creates a vacuum that draws medication into the reservoir, and advancing the plunger into the barrel forces the medication from the reservoir and out through the needle. The syringe barrel 402 is shown marked with indicia 100, and specifically, patient body weight indicia 103 and the medication unit of measurement in mg 107. In a particular embodiment, the seal 404 may be colored for enhancing the visual identification thereof through the barrel, and in another embodiment may be made from or include a material that exhibits fluorescence in natural light or upon exposure to light outside of the visible spectrum (e.g. ultraviolet light, infrared, etc.) to assist in the visible accuracy obtained in preparing and verifying the dosage per calibration scale.

The plunger 401 is marked with plunger indicia (e.g., embossed text, recessed text, printed text) shown generally at reference numeral 405. The plunger indicia 405 can include detailed information indicating the medication or medication type represented as "xxxxxxxxxxx" shown at reference numeral 406, the medication unit of measurement appropriate per unit of patient characteristic (e.g., patient body weight) shown at reference numeral 408, as well as warning indicia indicating to the user that the syringe is not suitable for use with other medications and/or patients. The barrel and plunger indicia may be provided on one or more "sides" of each component such that the indicia is visibly apparent to the user regardless of how the syringe is held or handled.

Figure 4B:
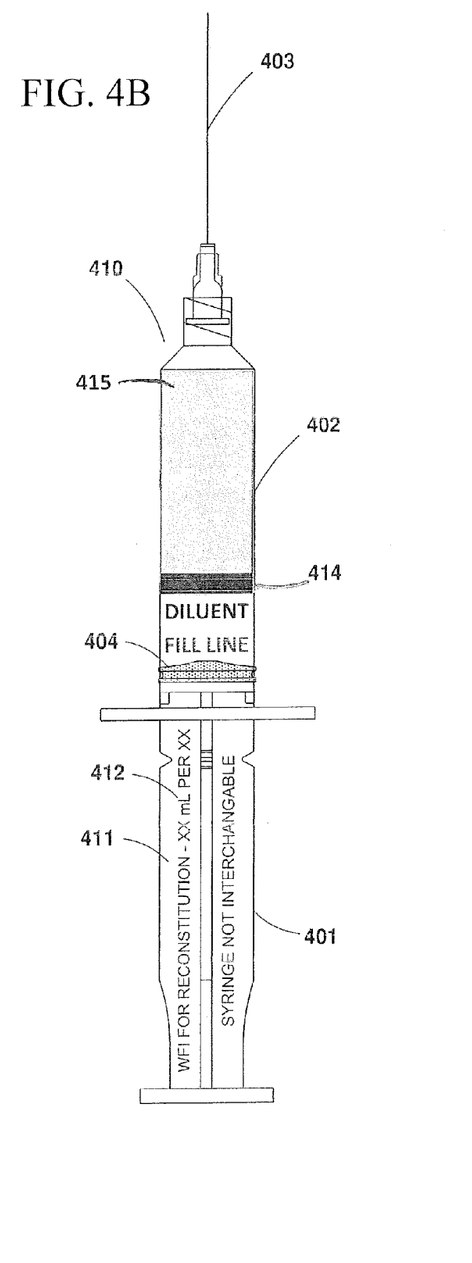
FIG. 4B illustrates one embodiment of a diluent syringe.
Figure 4C:
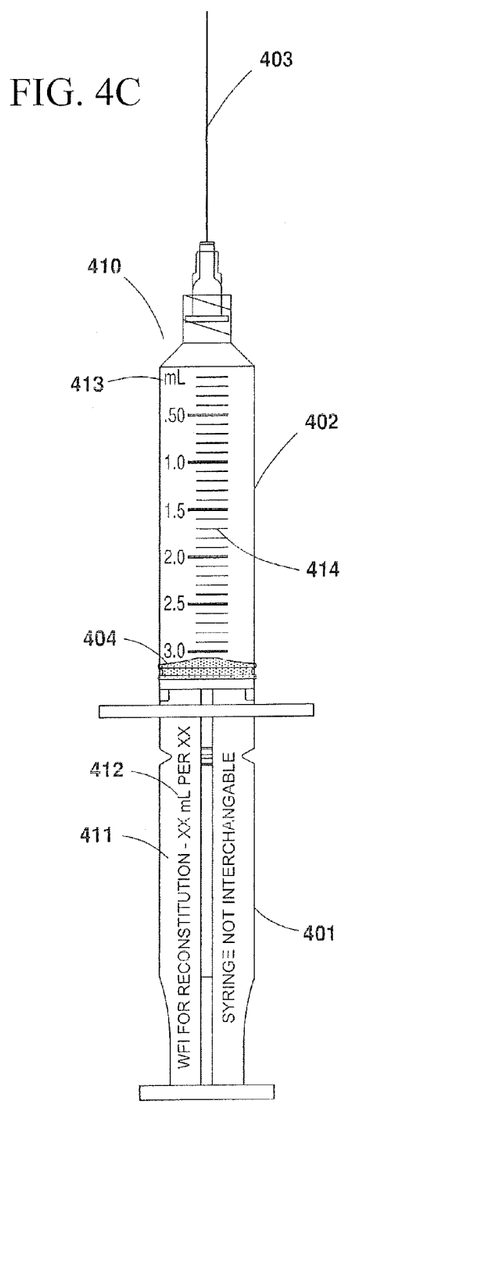
FIG. 4C illustrates another embodiment of a diluent syringe.

Referring to FIGS. 4B and 4C, embodiments of calibrated diluent syringes are shown generally at reference numeral 410. The diluent syringes 410 each generally include a plunger 401 having a seal 404, a barrel 402, and a needle 403. The plunger 402 may be marked with indicia indicating that the syringe is intended for use in reconstituting medication or a specific medication, shown at reference numeral 411, marked with indicia 412 indicating the unit of measurement per other unit of measurement (e.g., mL per mg), shown at reference numeral 412, and indicia indicating that the diluent syringe is not suitable for use with or interchangeable with other diluents and/or medications.

Referring specifically to FIG. 4B, the barrel 402 of the syringe 410 may be pre-calibrated and include an error-proof diluent fill line shown at reference numeral 414. The diluent fill line 414 may be marked with a readily visible annular ring around the barrel. In addition, or in the alternative, the predetermined "finable" portion of the reservoir may be opaque, tinted or colored to indicate to the user the portion of the internal reservoir to be filled with diluent for reconstituting the medication. In the particular embodiment shown in FIG. 4B, the fill level is indicated by both tinting the barrel and marking the fill line with a thick annular band. Thus, the diluent syringe 410 shown in FIG. 4B is pre-calibrated to be filled to only one predetermined volume, and thus does not require any measurement units or graduation markings.

Referring specifically to FIG. 4C, the diluent syringe 410 may be marked with units of measurement (e.g., mL) of diluent, and thus may be filled with varying amounts of diluent dependent on the medication and reconstitution instructions provided with the particular medication. As shown, the units are provided in mL as shown at reference numeral 413, and corresponding graduations are indicated by the graduation lines shown at reference numeral 414.

Figure 5:
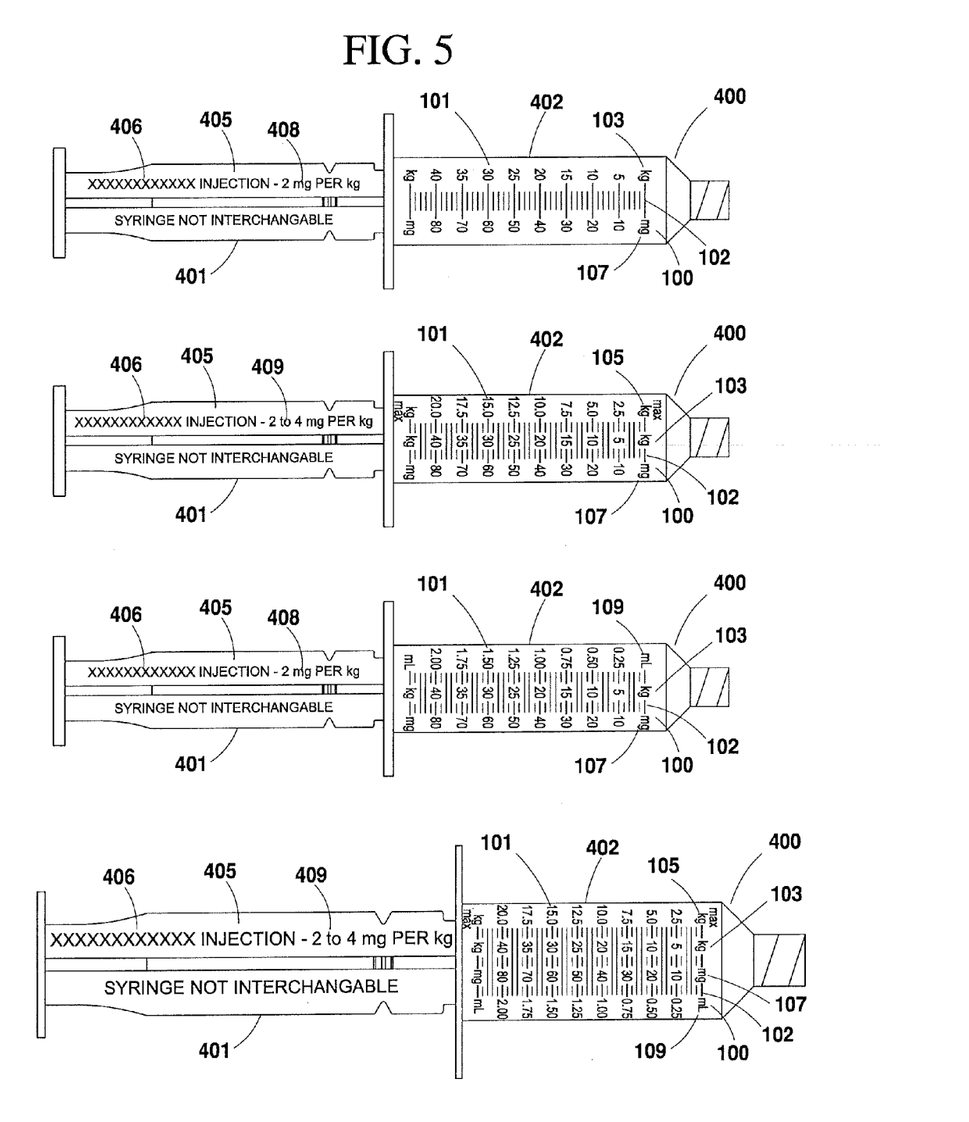
FIG. 5 illustrates various embodiments of syringes including indicia with dosages based on correlations between one or more of patient weight and medication volume and/or mass.

Referring to FIG. 5, various embodiments of pre-calibrated syringes are shown generally at reference numeral 400. The syringes 400 each generally include a plunger 401 and syringe barrel 402, each of which include some form of indicia for presenting information to the user. The plunger 401 of each syringe includes indicia indicating the medication or medication type, shown at reference numeral 406, the unit of measurement of medication per unit of body weight, shown at reference numeral 408, and indicia indicating that the syringe is not suitable for use with other medications, medication types or patients.

The syringe barrels 402 include indicia 100, such as various combinations of patient characteristics and medication measurement units 101 depending on the particular application, patient and medication to be administered. As shown, patient characteristics 103 may be marked using units of body weight (e.g., kg), or maximum kg shown at 105. Concentrations corresponding to the patient characteristic are shown at reference numeral 107, and medication volume corresponding to the patient characteristic are shown at reference numeral 109. Graduations are shown at reference numeral 102. The user may refer to one or more of the patient characterisitic, concentration indicia and volumetric indicia when loading the syringe, per the recommended dosage instructions. Thus, the user may know to fill the syringe with the appropriate amount of medication based on one or more of the patient characteristic and their own body weight, medication concentration and medication volume. The syringes 400 present to the user several key visual aids that help to avoid, for example, administration errors in the dosage of the medication, the use of the medication itself, the strength of the medication, etc.

Figure 6A:
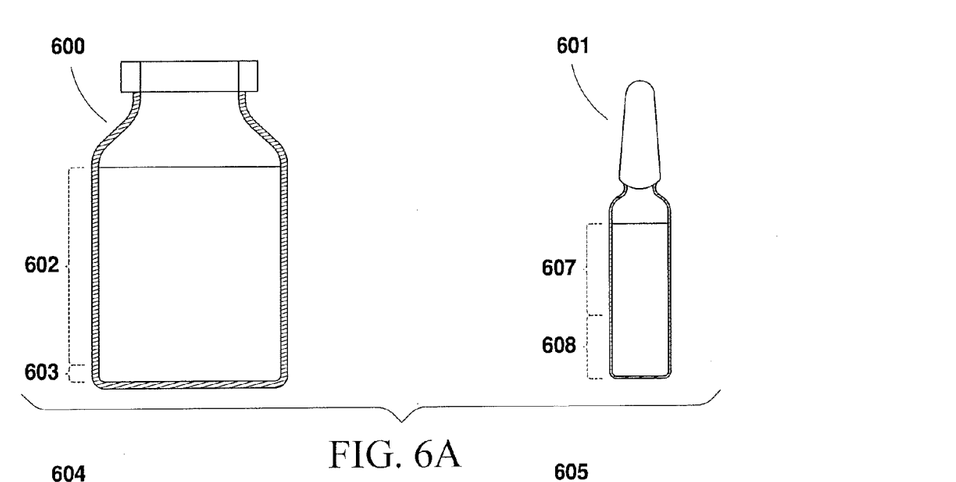
FIG. 6A illustrates embodiments of pre-filled vials.
Figure 6B:
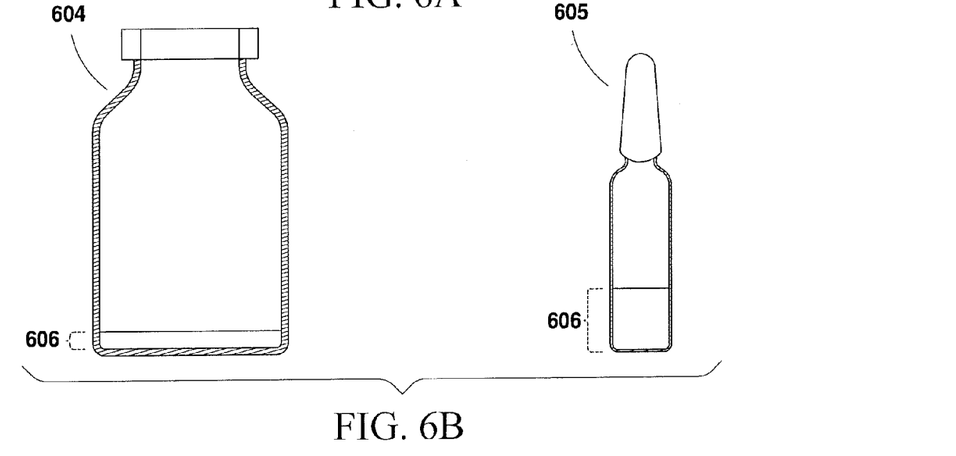
FIG. 6B illustrates another embodiment of pre-filled vials.
Figure 6C:
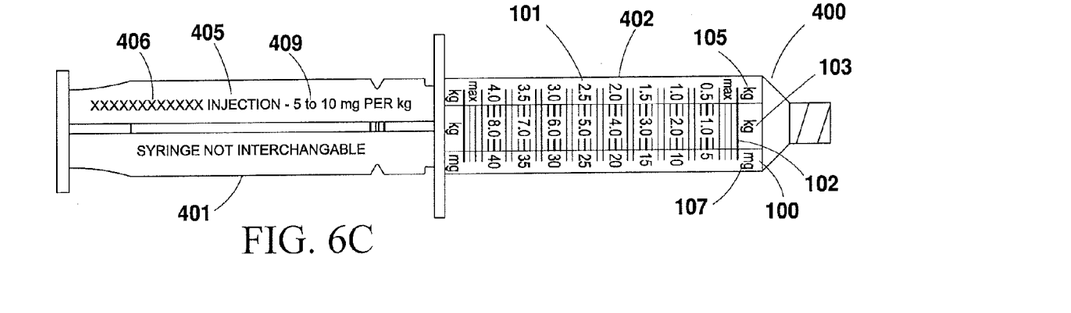
FIG. 6C illustrates another embodiment of a syringe having indicia indicating dosages based on correlations between patient weight and medication mass.

Referring to FIG. 6A, an exemplary 500 mg vial is shown at reference numeral 600, and an exemplary 100 mg ampoule is shown at reference numeral 601. Both the vial 600 and ampoule 601 contain prescribed amounts of medication indicated at reference numerals 603 and 608, respectively, as well as excess (i.e., waste) amounts of medication indicated at reference numerals 602 and 607, respectively. For example, a low dose pediatric or reduced-weight patient dosage injection may be 5 mg/kg for an 8 kg patient, thus requiring 40 mg, indicated at reference numeral 603. The remainder is thus waste. In comparison, FIG. 6B illustrates a vial 604 and ampoule 605 filled with only the prescribed amounts 606 and 606, respectively, thus there is no medication waste in the vial 604 and ampoule shown in FIG. 6B. These pre-filled vials and ampoules may be used in kits with corresponding syringes to reduce waste and avoid errors associated with improper dosing. FIG. 6C shows a volumetrically calibrated syringe 400 specifically correlated to the medication in the kit, and volume-scaled small dose patient range (such as the amount represented by 606 in FIG. 6B) to correlate with the vial or ampoule medication dosage strength of 5 mg/kg for pediatric range weights of from about 0.5 to about 8.0 kg.

Figure 7A:
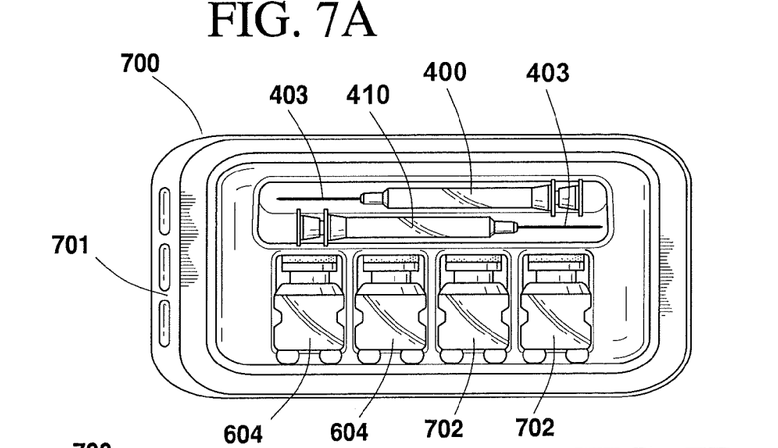
FIG. 7A illustrates a kit including a medication syringe, a diluent syringe and pre-filled vials.
Figure 7B:
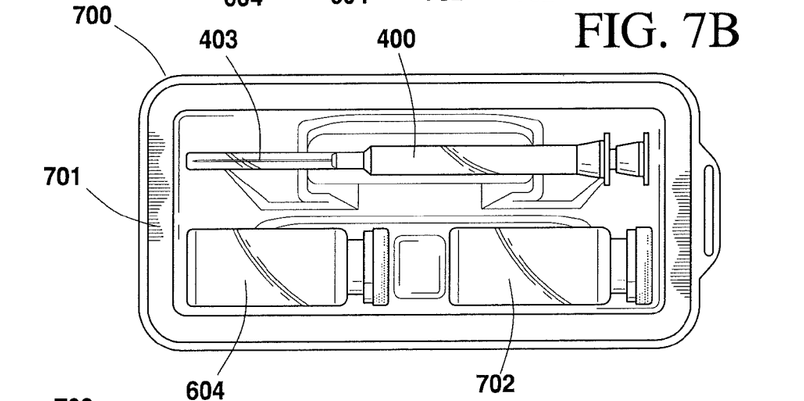
FIG. 7B illustrates a kit including a syringe and pre-filled vials.
Figure 7C:
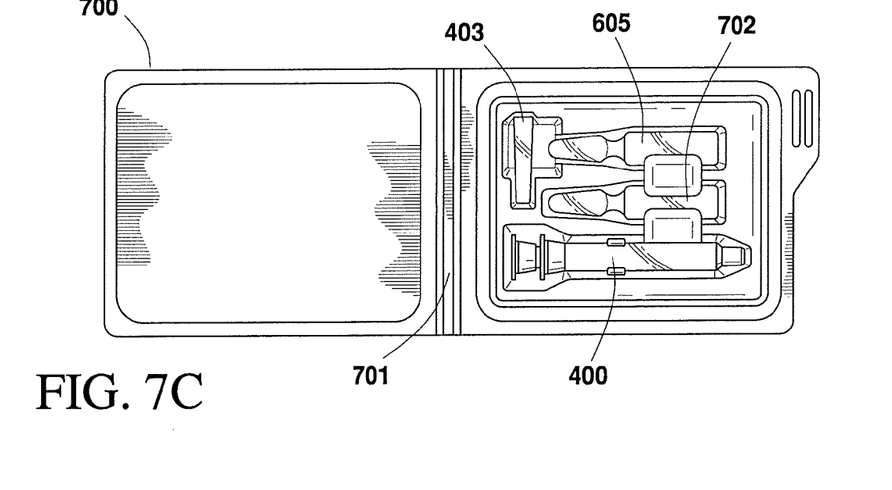
FIG. 7C illustrates another embodiment of a kit including a syringe, pre-filled vials and a removable needle.

FIGS. 7A-C illustrate various embodiment of pre-packaged kits 700 including one or more of a medication syringe 400, diluent syringes 410, pre-filled medication vials 604, and diluent vials 702. Referring to FIG. 7A, the pre-packaged combination kit includes a single, patient calibrated medication syringe 400 having a needle 403, a single, calibrated diluent syringe 410 having a needle 403, a plurality of pre-filled medication vials 604 filled with a predetermined amount of medication specific to the patient and patient characteristic, and a plurality of diluent vials 702 for reconstituting the medication. Referring to FIG. 7B, the kit 700 may include a single medication syringe 400, diluent vial 702 for reconstitution, and medication vial 604. Referring to FIG. 7C, the kit 700 may include a medication syringe 400, needle 403, pre-filled medication ampoule 605, and diluent ampoule 702. The pre-packaged kits containing a reconstitutable medication may have identifying features that would enable the user to clearly identify the correct diluent syringe for the corresponding diluent(s) and, additionally, the correct syringe for the corresponding medication. The identifying features or marks may, for example, include coloring the diluent syringe and the diluent container with one color (e.g., blue), and coloring the medication syringe and medication container with a different color (e.g., red), to avoid any confusion. Other corresponding and distinguishing marks for linking the diluent and diluent syringe and distinguish from the medication syringe and medication vials may include text, labels, symbols, etc.

The kits may further include packaging 701 that is preferably tamper-resistant and tamper evident. Packaging 701 may be in the form of blister packs, clamshell designs, etc. The packaging 701 is preferably made from sterilizable materials including, but not limited to, plastics such as high density polyethylene (HDPE), polyethylene terephthalate (PET), polycarbonate, etc., although the packaging could be made from another environmentally friendly material such as, for example, a starch or cellulose, etc.

Figure 8A:
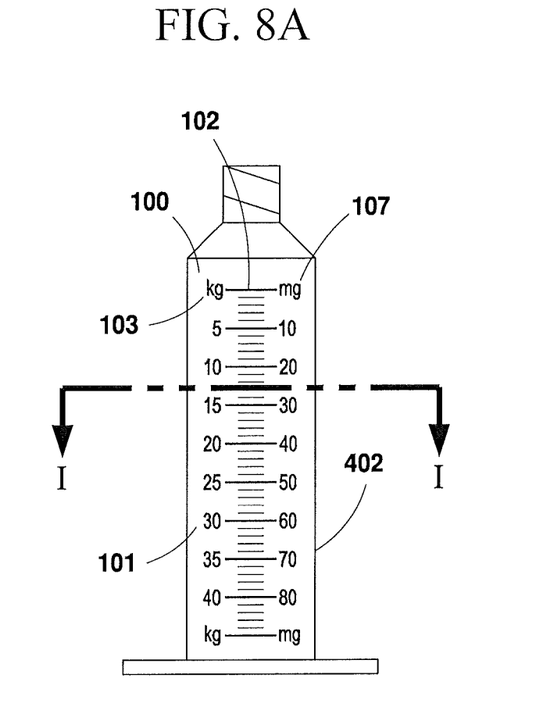
FIG. 8A illustrates a syringe barrel having correlating patient weight and medication mass dosage indicia.
Figure 8B:
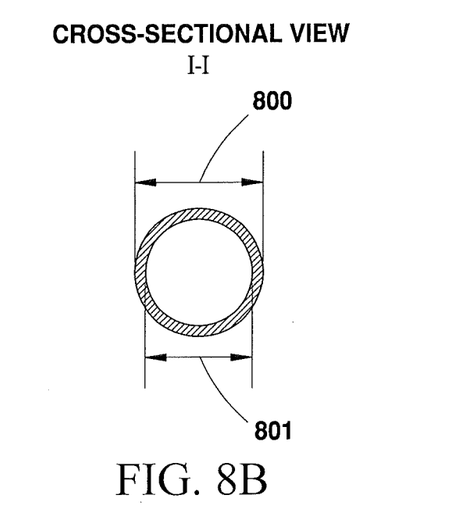
FIG. 8B is a cross-sectional view through the syringe barrel of FIG. 8A taken along line I-I.

Referring to FIG. 8A, another embodiment of a calibrated syringe barrel 402 is shown. The syringe barrel again includes indicia 100 corresponding to dosages based on patient weight 103, corresponding concentration indicia 107, and graduations 102. Referring to FIG. 8B, the wall thickness of the barrel 402 is relatively "standard," meaning that the inner wall diameter 801 is only slightly less than the outer wall diameter 800. FIGS. 8A and 8B thus shown an "industry standard" syringe having the look and feel that a user expects, as well as sufficient surface area on the barrel for indicating the patient characteristic measurements, medication units and graduations.

Figure 9A:
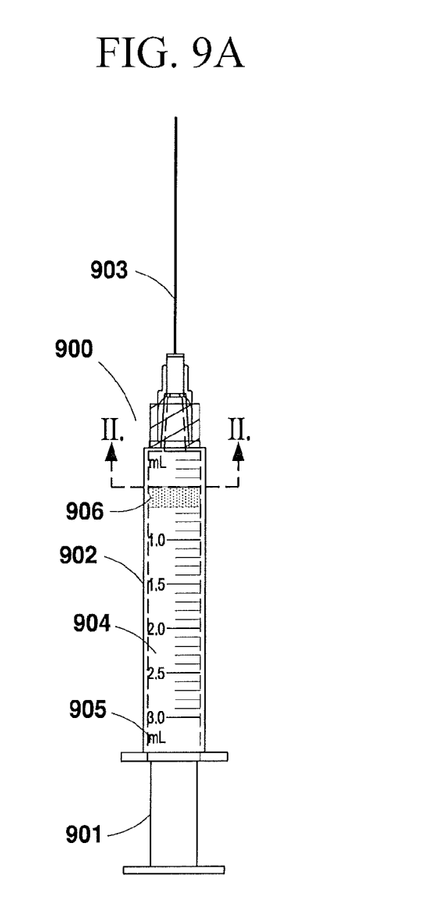
FIG. 9A illustrates a syringe having a thin wall thickness according to an embodiment of the invention.
Figure 9B:
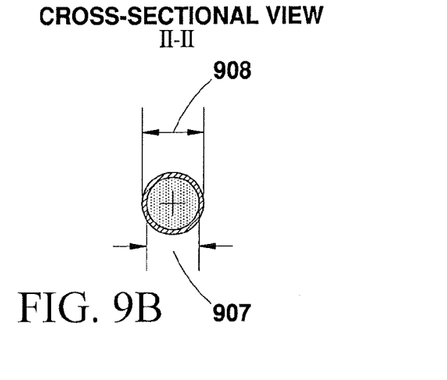
FIG. 9B is a cross-sectional view through the syringe of FIG. 9A taken along line II-II.

Referring to FIGS. 9A and 9B, an embodiment of a diluent syringe having a "standard" wall thickness is shown. For example, the syringe 900 is an industry standard 3 mL syringe. The syringe 900 generally includes a plunger 901, a syringe barrel 902, and a needle 903. Measuring indicia 904 may be provided on the inner surface of the barrel 902, the outer surface of the barrel, or the barrel may be manufactured to position the indicia at a pre-selected distance located between the inner and outer surface of the barrel, or on any combination of surfaces thereof. The measuring indicia preferably correspond to the volume of the syringe, indicated at reference numeral 905 in mL. Plunger 901 includes a seal 906 at one end thereof for effecting a seal between the end of the plunger and the inner wall of the barrel 902. The position of the seal 906 along the length of the barrel 902 indicates the volume of fluid within the syringe. Referring to FIG. 9B, the inner diameter of the barrel shown at reference numeral 907 is only slightly less than the outer diameter of the barrel shown at reference numeral 908, thus the barrel has a relatively "thin," industry standard wall thickness.

Figure 10A:
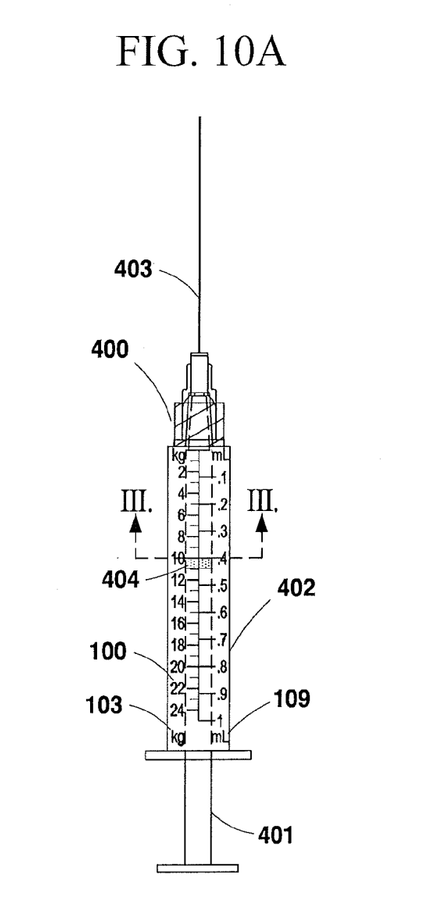
FIG. 10A illustrates a syringe having a thick wall thickness according to an embodiment of the invention.
Figure 10B:
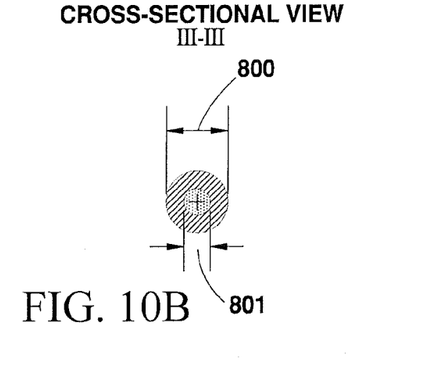
FIG. 10B is a cross-sectional view through the syringe of FIG. 10A taken along line III-III.

Referring to FIG. 10, another embodiment of a pre-calibrated medication syringe is shown generally at reference numeral 400. Again, the syringe generally includes a plunger 401 having an elastomeric sealing member 404, a barrel 403, a needle 403, indicia 100 including patient, characteristic indicia 103 represented in kg, volumetric indicia 109 represented in mL, and graduations. In contrast to the syringe and corresponding "standard" wall thickness shown in FIGS. 8A and 8B, the syringe and corresponding wall thickness in FIGS. 10A and 10B is noticeably thicker. In other words, referring to FIG. 10B, the inner wall diameter 801 is substantially less than the outer wall diameter 800, resulting in a relatively large wall thickness and lesser volume internal reservoir. This specific syringe configuration is suitable for use in applications in which a lesser predetermined volume of medication is needed, but it is desirous to maintain the feel of an industry standard syringe as well as provide more precise patient characteristic targeted indicia with increased graduations for lower volume and dosage measurement thus creating a more precise dosage. In addition the creating substantial surface area on the barrel for locating the patient characteristic and/or measurement indicia. The syringe shown in FIGS. 10A and 10B is thus particularly suited for small volume injections while still providing the feel of an accepted, larger diameter syringe and good visibility.

The syringe embodiments disclosed herein may be volumetrically calibrated and their indicia adjusted for the dosage strength of the particular medication appropriate for a patient in a specific weight range, $m^2$, or dosage range. This provides a clearer and more gradient-correlated dosage-to-weight or BSA ($m^2$) calibrated indicia for precise dosages than standard non-calibrated industry syringes. This feature permits the volume to be calibrated and measured in a smaller, more precise, gradient indicia scale for lower incremental doses, such as dosages for infants, pediatric patients, and other patients who are unusually sensitive to the medication as well as for the injection of extremely potent and dangerous medications such as pain management, anesthetics, biologics and oncology drugs than standard non-calibrated industry syringes.

The syringes, diluent syringes, pre-filled vials and combination kits disclosed herein substantially eliminate the human errors associated with the consolidation of components, correlation of components and the computations ordinarily conducted by healthcare professionals in connection with performing dosage-to-patient weight or body surface area calculations, provided the user follows the pre-calibrated indicia on the syringe. The pre-packaged kits disclosed herein containing reconstitutable medication, the corresponding diluent(s), and the pre-calibrated syringe(s) for the medication substantially eliminate multiple methods and procedures that are the leading direct cause of MAEs from injectable administration. The combination kits substantially eliminate user procedures and methods ordinarily conducted by healthcare professionals, specifically, the collection of the correct medication for patient and patient class, the correct corresponding diluent(s) for a particular medication, the syringe and needle for the particular route of administration, the correct calculations, measurements and procedures for the correct reconstitution of the medication by the diluent(s), the calculation determination of dosage-to-patient weight or BSA, and the subsequent verification of these procedures prior to the injection. The removal of these procedures and methods substantially eliminates the risk of human errors. This, in turn, substantially eliminates the primary causes of MAEs associated with injectable medications.

Additional embodiments contemplate allowing the dosage to patient weight calibrated measurement indicia on the syringe to uniquely target specific weight scales, customized for adult, pediatric, or infant weight, etc. The calibrated measurement indicia scale would thereby allow better visibility as it is specifically focused on a particular weight and patient range allowing for more accurate incremental dosages and less over all waste through this volume-scaled patient range calibration.

Embodiments of the present invention can include a single-use syringe that is pre-filled at the time of manufacture with a pre-determined volume of a particular medication. The specific dosage of the particular medication could then be administered according to the calibrated measurement indicia that is pre-calculated based on the weight of the patient or body surface area and the correlating dosage. This further allows the user to see the dosage of the subject medication in one calibrated measurement indicia that specifically correlates to another calibrated measurement indicia corresponding to the patient's weight or body surface area. This provides critical safety verification during the preparation and administration of the medication.

Further embodiments contemplate a system, kit and syringe with calibrated measurement indicia and volumetric design comprising a pre-determined, pre-filled volume of the medicine pre-calculated and specifically correlated from the volume dosage strength (mcg, mg, mL, IU, cc) to the patient weight or body surface area (g, kg, lb, $m^2$) based on the particular manufacturers suggested drug product dosage schedule to correlate the syringe that may comprise a substantially permanent indicia indicating solely weight or body surface area of the patient, corresponding with that particular manufacturers injectable drug product dosage schedule. In this regard, the user does not need to perform any calculations to determine the proper dosage. The user must merely know the weight or body surface area of the patient and then use the syringe designed for a patient of such weight range.

Modifications, variations, and other embodiments of the present invention may come to the mind of one skilled in the field to which this invention pertains, having the benefit of the teachings presented in the foregoing descriptions. Therefore, it is to be understood that the invention is not to be limited to the specific embodiments disclosed and that modifications are intended to be included within the scope of the appended claims.

What is claimed is:

1. A syringe calibrated for use with a predetermined medication, comprising:
    a barrel having an internal reservoir volumetrically calibrated to contain a volume of the predetermined medication;
    a plunger received within the barrel and axially moveable relative thereto to change the volume of the predetermined medication in the reservoir;
    a first set of graduated indicia marked on the barrel indicating a predetermined patient characteristic calibrated to a manufacturers recommended volumetric dosage for the predetermined medication;
    a second set of graduated indicia marked on the barrel indicating volumetric dosage of the predetermined medication;
    diluent indicia marked on the barrel indicating a calibrated volume of diluent required to reconstitute the predetermined medication; and
    graduation lines marked on the barrel indicating the first set of graduated indicia and the second set of graduated indicia.

2. The syringe according to claim 1, wherein the predetermined patient characteristic is selected from the group consisting of patient body weight and patient body surface area.

3. The syringe according to claim 1, wherein the volumetric dosage is selected from the group consisting of volume, mass and concentration of the medication.

4. The syringe according to claim 1, further comprising indicia marked on the plunger indicating the name of the predetermined medication for use with the syringe.

5. The syringe according to claim 4, further comprising indicia marked on the plunger indicating a correlation between a unit of measurement of the predetermined medication and a unit of measurement of the predetermined patient characteristic.

6. The syringe according to claim 1, wherein the volumetric dosage of the predetermined medication calibrated based on the predetermined patient characteristic is expressed as at least one of a manufacturer's recommended maximum dosage and a manufacturer's recommended dosage of the predetermined medication.

7. The syringe according to claim 1, wherein the internal reservoir diameter is dependent on the volumetric dosage of the predetermined medication determined based on the predetermined patient characteristic or a predetermined patient characteristic range.

8. The syringe according to claim 1, further comprising a needle attached to one end of the barrel and in fluid communication with the internal reservoir.

9. A pre-packaged medication kit, comprising:
- a medication syringe calibrated for use with a predetermined medication including a first set of graduated indicia marked on the barrel indicating a predetermined patient characteristic calibrated to a manufacturers recommended volumetric dosage for the predetermined medication, a second set of graduated indicia marked on the barrel indicating volumetric dosage of the predetermined medication, and graduation lines marked on the barrel indicating the first set of graduated indicia and the second set of graduated indicia;
- a pre-filled medication container containing a predetermined volume of the predetermined medication; and
- a diluent syringe for reconstituting the predetermined medication including indicia marked on a barrel thereof indicating a calibrated volume of diluent required to reconstitute the predetermined medication.

10. The pre-packaged medication kit according to claim 9, wherein the predetermined patient characteristic is selected from the group consisting of patient body weight and patient body surface area.

11. The pre-packaged medication kit according to claim 9, wherein a plunger of each of the medication syringe and the diluent syringe is marked with indicia indicating the predetermined medication name or diluent for use therewith, and wherein the plunger of the medication syringe is marked with indicia indicating a correlation between a unit of measurement of the predetermined medication and a unit of measurement of the predetermined patient characteristic, and wherein the plunger of the diluent syringe is marked with indicia indicating a correlation between diluent volume and a unit of measurement of the predetermined medication.

12. The pre-packaged medication kit according to claim 9, wherein the indicia on the diluent syringe is an annular barrel marking indicating a diluent fill line.

13. The pre-packaged medication kit according to claim 12, wherein a barrel of the diluent syringe is tinted from a needle end of the barrel to the diluent fill line to provide a visible indicator to the user of the volume of diluent to be drawn into the diluent syringe.

14. The pre-packaged medication kit according to claim 9, wherein the volumetric dosage of the predetermined medication calibrated based on the predetermined patient characteristic is expressed as at least one of a manufacturer's recommended maximum dosage and a manufacturer's recommended dosage of the predetermined medication.

* * * * *